United States Patent [19]
Simpson

[11] Patent Number: 5,269,793
[45] Date of Patent: Dec. 14, 1993

[54] GUIDE WIRE SYSTEMS FOR INTRAVASCULAR CATHETERS

[75] Inventor: John B. Simpson, Palo Alto, Calif.

[73] Assignee: Devices for Vascular Intervention, Inc., Redwood City, Calif.

[21] Appl. No.: 35,518

[22] Filed: Mar. 22, 1993

Related U.S. Application Data

[63] Continuation of Ser. No. 697,913, May 1, 1991, abandoned, which is a continuation of Ser. No. 382,866, Jul. 20, 1989, abandoned.

[51] Int. Cl.$^5$ .............................................. A61B 17/22
[52] U.S. Cl. .................... 606/159; 606/180; 606/194; 604/95; 604/96; 604/170
[58] Field of Search ............. 128/657, 658, 772; 604/95, 96, 102, 103, 164, 170, 280, 281, 282; 606/7, 159, 180, 194, 170

[56] References Cited

U.S. PATENT DOCUMENTS

| | | | |
|---|---|---|---|
| 4,020,829 | 5/1977 | Willson et al. | 604/95 |
| 4,215,703 | 8/1980 | Willson . | |
| 4,323,071 | 4/1982 | Simpson et al. . | |
| 4,444,186 | 4/1984 | Wolvek et al. . | |
| 4,571,240 | 2/1986 | Samson et al. . | |
| 4,582,181 | 4/1986 | Samson . | |
| 4,586,923 | 5/1986 | Gould et al. . | |
| 4,596,563 | 6/1986 | Pande . | |
| 4,627,436 | 12/1986 | Leckrone . | |
| 4,669,469 | 6/1987 | Gifford, III et al. . | |
| 4,682,607 | 7/1987 | Vaillancourt et al. . | |
| 4,724,846 | 2/1988 | Evans, III . | |
| 4,771,774 | 9/1988 | Simpson et al. . | |
| 4,771,776 | 9/1988 | Powell et al. . | |
| 4,775,371 | 10/1988 | Mueller, Jr. . | |
| 4,784,639 | 11/1988 | Patel | 128/658 |
| 4,794,931 | 1/1989 | Yock | 128/662.06 |
| 4,808,164 | 2/1989 | Hess | 606/7 |
| 4,819,634 | 4/1989 | Shiber | 604/95 |
| 4,820,349 | 4/1989 | Saab | 604/96 |
| 4,842,579 | 6/1989 | Shiber | 606/159 |
| 4,894,051 | 1/1990 | Shiber | 606/159 |
| 4,911,170 | 3/1990 | Thomas, III et al. | 128/662.06 |
| 4,921,483 | 5/1990 | Wijay et al. | 604/96 |
| 4,927,413 | 5/1990 | Hess | 606/7 |
| 5,026,366 | 6/1991 | Leckrone | 606/7 |
| 5,047,040 | 9/1991 | Simpson et al. | 606/159 |
| 5,071,425 | 12/1991 | Gifford, III et al. | 606/159 |
| 5,078,723 | 1/1992 | Dance et al. | 606/159 |
| 5,084,010 | 1/1992 | Plaia et al. | 606/159 |

FOREIGN PATENT DOCUMENTS

| | | |
|---|---|---|
| 0163502 | 12/1985 | European Pat. Off. . |
| 0277369 | 8/1988 | European Pat. Off. . |
| WO89/02763 | 4/1989 | PCT Int'l Appl. . |
| 658195A5 | 10/1986 | Switzerland . |
| 2175505A | 12/1986 | United Kingdom . |

*Primary Examiner*—Ralph Lewis
*Attorney, Agent, or Firm*—Townsend and Townsend Khourie and Crew

[57] ABSTRACT

A vascular catheter comprises a catheter body having a fixed guide wire secured to its distal end. The fixed guide wire includes an axial passage which is aligned with a wire lumen within the catheter body so that the vascular catheter can be introduced to the vascular system over a movable guide wire. The catheter body typically comprises flexible tube having a housing secured to its distal end. A variety of interventional devices, including both therapeutic and diagnostic devices, can be disposed within the housing. Use of both a fixed guide wire and a movable guide wire facilitates initial introduction of even large diameter vascular catheters, while allowing subsequent repositioning of the catheters after the movable guide wire has been withdrawn.

41 Claims, 2 Drawing Sheets

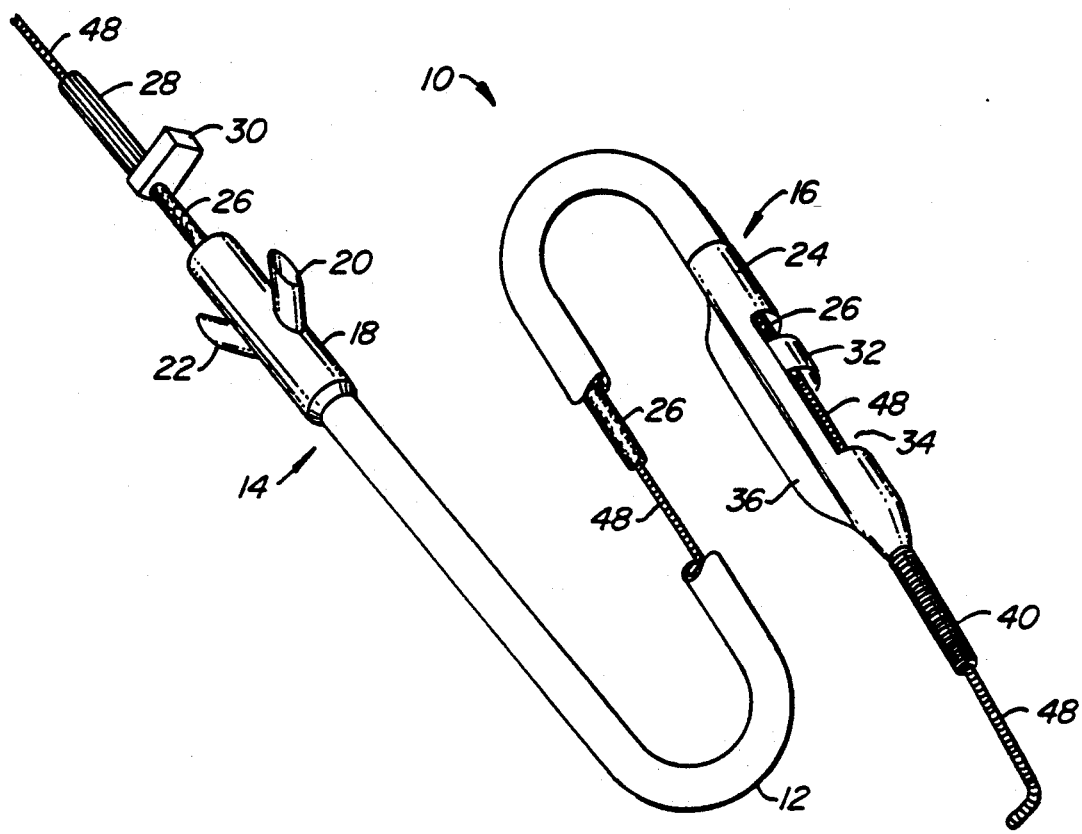
FIG._1.
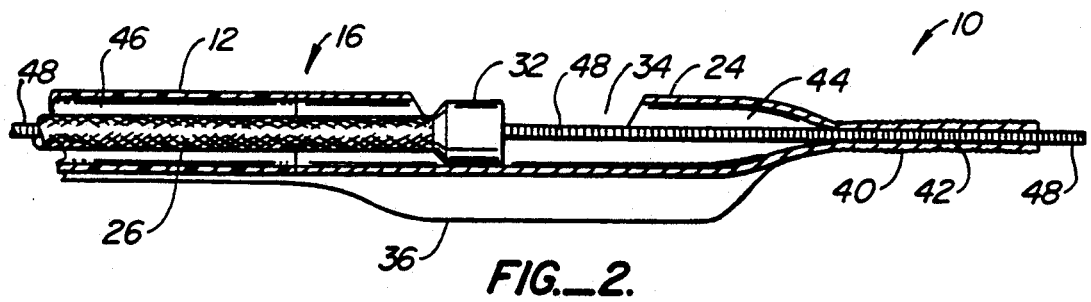
FIG._2.
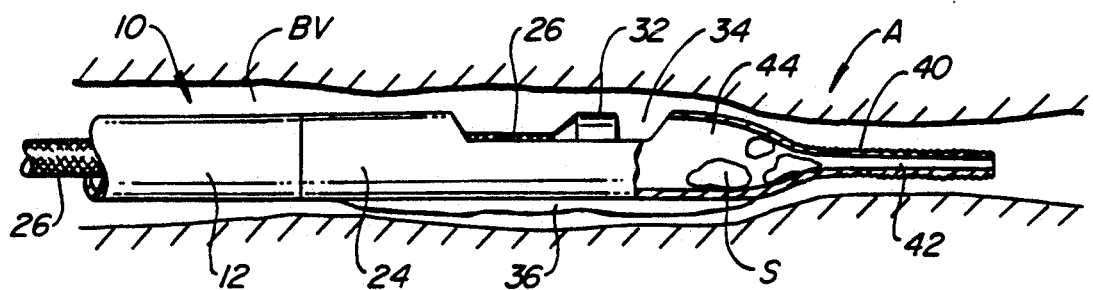
FIG._3.

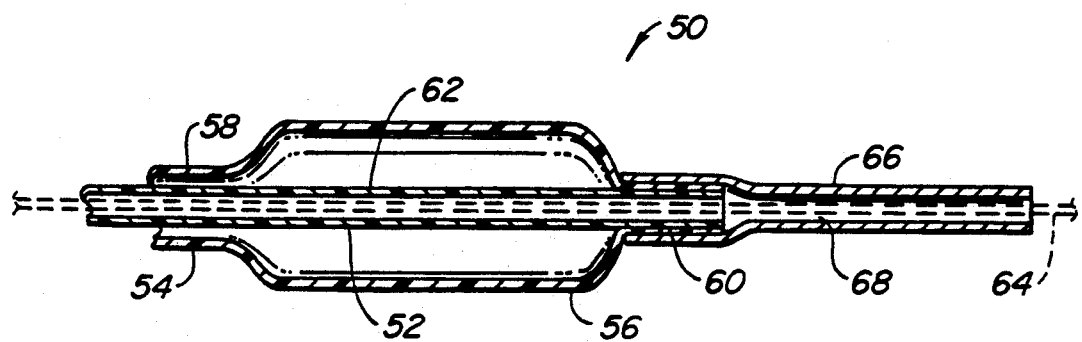
FIG._4.
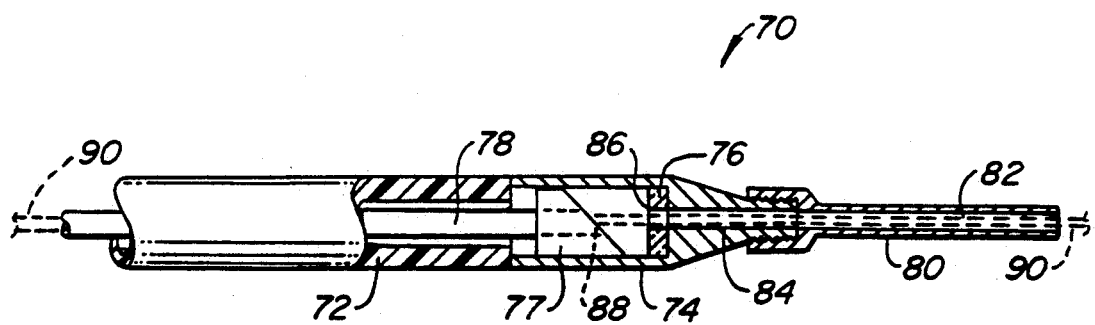
FIG._5.

GUIDE WIRE SYSTEMS FOR INTRAVASCULAR CATHETERS

This is a continuation of application Ser. No. 07/697,913, filed May 1, 1991, now abandoned which is a continuation of Ser. No. 07/382,866 filed Jul. 20, 1989, now abandoned.

BACKGROUND OF THE INVENTION

1. Field of the Invention

The present invention relates generally to the construction and use of vascular catheters. More particularly, the invention relates to intravascular catheters and catheter systems employing both a fixed guide wire and a movable guide wire for positioning within the vascular system.

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed the limbs of the body and coronary blood vessels which feed the heart. When deposits accumulate in localized regions of a blood vessel, blood flow is restricted and the person's health is at serious risk.

Numerous approaches for reducing and removing such vascular deposits have been proposed, including balloon angioplasty where a balloon-tipped catheter is used to dilate a region of atheroma, atherectomy where a blade or other cutting element is used to sever and remove the atheroma, and laser angioplasty where laser energy is used to ablate at least a portion of the atheroma. In addition to such therapeutic approaches, a variety of techniques for transluminal imaging of atheroma and other diseased regions of the blood vessel have been proposed, including endoscopic imaging techniques and ultrasonic imaging techniques.

With all such techniques, it is necessary to position a vascular catheter at a desired location within the blood vessel to be treated or imaged. Heretofore, two alternative approaches have generally been employed for such positioning. In the first approach, the vascular catheter is provided with a "fixed guide wire" secured to its distal end. The fixed guide wire is typically a coiled spring or other elongate resilient member having a preformed, curved tip. The catheter can be guided through branches within the vascular network by rotating the entire catheter, causing the tip of the guide wire to enter a desired branch as the catheter is moved forward.

In the second technique, an entirely separate "movable guide wire" is employed. The movable guide wire is itself a coiled spring or other resilient elongate member and includes a curved tip similar to that provided on the fixed guide wires described above. The vascular catheter being positioned includes a wire lumen which is sized to receive the movable guide wire. The movable guide wire is first positioned within the vascular system so that its distal end extends beyond the region of interest. The vascular catheter is then inserted over the movable guide wire using the wire lumen. Such procedures using movable guide wires are commonly referred to as "over-the-wire" insertional techniques.

Each approach for catheter insertion has advantages and disadvantages. The fixed guide wire system is advantageous in that it requires fewer steps for insertion, there is no separate guide wire present to interfere with the diagnostic and/or therapeutic procedure being performed, and the guide wire remains in place to allow for repositioning of the catheter at later stages of the procedure. The movable guide wire is advantageous in that it facilitates positioning of even large diameter catheters which would be difficult to manipulate using a fixed guide wire.

The disadvantages of each type of guide wire system are largely the opposites of the advantages. The fixed guide wire systems are difficult to manipulate and generally unsuitable for large diameter catheters, while the movable guide wire systems must generally remain in place to allow for subsequent repositioning of the catheter during the diagnostic or therapeutic procedure. The presence of the movable guide wire can interfere with the procedure and occupies limited space within the catheter which might otherwise be advantageously employed.

It would therefore be desirable to provide catheter constructions and insertional methods which can provide the benefits associated with both the fixed guide wire and movable guide wire systems, without the associated disadvantages. In particular, it would be desirable to provide catheters which can initially be positioned using a movable guide wire but which remain positionable even after withdrawal of the movable guide wire.

2. Description of the Background Art

U.S. Pat. No. 4,669,469 and European Patent Application 163 502, the disclosures of which are incorporated herein by reference, each describe atherectomy catheters comprising a distal housing having an axially translatable blade therein. The catheters are shown to have fixed guide wires or movable guide wires, but not both. U.S. Pat. No. 4,794,931, describes an ultrasonic imaging catheter, which is shown to employ a fixed guide wire for positioning. U.S. Pat. No. 4,597,755, describes a large diameter balloon catheter having a coil spring within its distal end. The coil spring is intended to prevent kinking of the catheter, not to aid in positioning the catheter. U.S. Pat. No. 4,571,240, describes a balloon catheter having a radiopaque marker at the distal end of the catheter body. The distal tip of the catheter is elongated, but is not suitable to act as a fixed guide wire. U.S. Pat. No. 4,582,181, describes a balloon catheter having an integral guide wire which extends the entire catheter length. The guide wire terminates in a helical coil which is attached to the distal end of the catheter. Movable guide wires are described in U.S. Pat. Nos. 4,724,846; 4,682,607; and 4,215,703; the disclosures of which are incorporated herein by reference. U.S. Pat. No. 4,586,923, describes a curved tip catheter with a mechanism for selectively deflecting said tip. U.S. Pat. No. 4,596,563, describes a catheter having a flexible tip formed continuously with the catheter body. U.S. Pat. No. 4,636,346, describes a guiding catheter intended to facilitate the introduction of vascular catheters. See also, U.S. Pat. Nos. 4,775,371; 4,677,436; and 4,627,436.

SUMMARY OF THE INVENTION

According to the present invention, vascular catheters are provided with a fixed guide wire in addition to the capability for receiving a movable guide wire. In this way, the vascular catheters can be initially positioned using an "over-the-wire" technique, facilitating the manipulation of even very large diameter catheters. After the catheter has been initially positioned, the movable guide wire can be withdrawn and the catheter subsequently repositioned using the remaining fixed guide wire. Thus, the present invention provides the benefits previously associated with both the fixed guide wire and movable guide wire catheter configurations. Additionally, the method of the present invention results in the wire lumen being available for other uses during the catheter procedure, for example perfusion or aspiration. In atherectomy devices, the fixed guide wire (which is hollow to receive the movable guide wire) further acts as a trap for severed atheroma which is collected in the tip of the catheter.

The catheter of the present invention comprises a catheter body having a lumen extending from a distal end to a proximal end. A fixed guide wire is secured to the distal end of the catheter body and includes an axial passage extending therethrough. Together the catheter body lumen and axial passage are capable of receiving a movable guide wire to facilitate initial positioning of the catheter system. The movable guide wire can then be removed, leaving the fixed guide wire available for subsequent repositioning of the catheter. The ability to reposition the catheter after withdrawal of the movable guide wire is particularly advantageous when the catheter is blocking a coronary artery, resulting in an ischemic reaction. The availability of the fixed guide wire allows the treating physician to pull back on the catheter to restore blood flow (relieving the ischemic condition) and then immediately repositioning the catheter using only the fixed guide wire.

In a first particular embodiment, the catheter body includes a flexible tube and a housing secured to the distal end of the flexible tube. The fixed guide wire is secured to the distal end of the housing, and the movable guide wire extends through the tube, housing, and axial passage in the guide wire for initial positioning. Usually, the housing will include an interventional or diagnostic element, such as a cutting blade, laser source, hot cap, ultrasonic transducer, or the like. In a second particular embodiment, an inflation balloon may be provided at the distal end of the catheter body for use in angioplasty procedures.

BRIEF DESCRIPTION OF THE DRAWINGS

FIG. 1 is an isometric view of a vascular atherectomy catheter system constructed in accordance with the principles of the present invention.

FIG. 2 is a detailed sectional view of the distal end of the catheter system of FIG. 1.

FIG. 3 is a partial sectional view of the distal end of the catheter of FIG. 1 shown in position within a blood vessel.

FIG. 4 is a sectional view of the distal end of an angioplasty balloon catheter constructed in accordance with the principles of the present invention.

FIG. 5 is a partial sectional view of the distal end of an ultrasonic imaging catheter constructed in accordance with the principles of the present invention.

DESCRIPTION OF THE SPECIFIC EMBODIMENTS

The present invention provides an improved method for introducing, positioning, and subsequently repositioning a catheter device within a patient's vascular system. The catheter of the present invention comprises a catheter body and a fixed guide wire secured to the distal end thereof, where the fixed guide wire includes an axial passage capable of receiving a movable guide wire. The catheter body usually comprises an elongate flexible tube having a housing secured to its distal end, where the fixed guide wire is secured to the housing. The flexible tube and housing together define a wire lumen which is open to the axial passage in the fixed guide wire, allowing the catheter to be inserted over a separate movable guide wire.

The method of the present invention comprises initially introducing the movable guide wire in a conventional manner so that the distal end of the movable guide wire lies proximate the region of interest within the vascular system. The catheter device is then inserted over the movable guide wire until the distal end or housing of the catheter reaches the same region of interest. The movable guide wire can then be removed, allowing use of the catheter without interference from the presence of a movable guide wire. The remaining fixed guide wire, however, allows subsequent repositioning of the catheter without the necessity of reintroducing the movable guide wire as has heretofore been required under certain circumstances. Additionally, after the movable guide wire has been withdrawn, the wire lumen can be used for other purposes, such as aspiration and perfusion.

The vascular catheters of the present invention can be used for a wide variety of purposes, including interventional and diagnostic techniques. Interventional catheters which can be constructed in accordance with the principles of the present invention include atherectomy catheters such as those described in U.S. Pat. No. 4,669,469 and European Patent Application 163 502, the disclosures of which have been previously incorporated herein by reference; balloon angioplasty catheters of the type described in U.S. Pat. No. 4,323,071, the disclosure of which is incorporated herein by reference, and laser ablation catheters of the type described in British Patent Application No. 2 175 505A, the disclosure of which is incorporated herein by reference. Diagnostic catheters which may be constructed in accordance with the principles of the present invention include endoscopic catheters and ultrasonic imaging catheters such as those described in U.S. Pat. No. 4,794,931, the disclosure of which is incorporated herein by reference.

Movable guide wires useful in the catheter systems of the present invention may be of any standard construction generally employed for the introduction of vascular catheters. Commonly, the movable guide wires will comprise helical wire coils formed over a core of tubing or solid wire. Such constructions are exemplified in U.S. Pat. Nos. 4,215,703 and 4,724,846, and the references cited therein, the disclosures of which are incorporated herein by reference. Alternatively, the movable guide wire may be formed using a stranded construction, as described in U.S. Pat. No. 4,682,607, the disclosure of which is incorporated herein by reference. In any of these constructions, the stiffness of the guide wire will typically vary over the length, with the guide wire being more flexible at its distal tip relative to the remaining length of the guide wire. Optionally, the guide wires may be coated with a material which facilitates introduction, such as polytetrafluoroethylene (PTFE), polyurethane, and the like.

The length and diameter of the movable guide wires of the present invention will vary depending on use, with the guide wires used for coronary procedures having lengths in the range from about 125 to 200 cm and diameters in the range from about 0.01 to 0.025 inches. Guide wires used in peripheral procedures will have lengths in the range from about 60 to 200 cm and diameters in the range from about 0.014 to 0.06 inches. The distal tip of the guide wire will typically be deflected or curved in order to facilitate manipulation and advancement of the guide wire through the vascular system in a conventional manner.

The fixed guide wires used in the catheter constructions of the present invention will be similar in certain respects to those of previous constructions, but will be modified in order to receive the movable guide wires as just described. In particular, the fixed guide wires of the present invention will include an axial passage that is open at its proximal end to a wire lumen formed within the catheter body. The axial passage will also be open at its distal end so that the movable guide wire is able to pass through the entire length of the fixed guide wire as well as the catheter body while the catheter is being introduced.

Both the external diameter of the fixed guide wire and internal diameter of the axial passageway will vary depending on the intended application of the catheter. For coronary procedures, the external diameter of the fixed guide wire will typically be in the range from about 0.016 to 0.05 inches, while the internal diameter will be in the range from about 0.012 to 0.03 inches. For peripheral procedures, the external diameter of the fixed guide wire will be in the range from about 0.02 to 0.06 inches, while the internal diameter of the axial passageway will be in the range from about 0.02 to 0.04 inches. The length of the fixed guide wire will generally be in the range from about 1 to 5 cm, more usually being in the range from about 2 to 3 cm. Normally, the fixed guide wire will be substantially straight in order to facilitate entry over the movable guide wire, although a certain degree of curvature or deflection is acceptable so long as it does not result in seizing or binding of the fixed guide wire as it is being inserted over the movable guide wire. In particular, when the fixed guide wire is formed from a lubricious material, such as a plastic as described below, curvature of the tip may be provided. The curvature will, however, be straightened when the fixed guide wire is placed over the movable guide wire. Generally, it is unnecessary to provide curvature or deflection in the fixed guide wire since it will not be used for moving the catheter through branches in the vascular system, but only for more limited movement within a single branch of a vascular system.

The fixed guide wire will generally be significantly more flexible than the catheter body to which it is attached. Usually, the fixed guide wire will be a helical coil, optionally being formed over a tube or a flattened safety ribbon which further defines the axial passage for receiving the movable guide wire. Alternatively, the fixed guide wire may be a metal bellows or may be a thermoplastic or thermoset plastic tube having a radiopaque filler, such as barium or bismuth.

Referring now to FIGS. 1-3, a catheter system 10 constructed in accordance with the principles of the present invention comprises a catheter body including a flexible tube 12 which extends from a proximal end 14 to a distal end 16. A proximal housing 18 is secured to the proximal end of flexible tube 12 and includes an inflation port 20 and a perfusion port 22. A distal housing 24 is secured to distal end 16 of the tube 12, and a drive member 26 extends from the proximal housing 18, through a central lumen of flexible tube 12, and into the distal housing 24. As illustrated, distal housing 24 is a rigid structure which can be formed of metal, for example, stainless steel. Drive member 26 terminates in a coupling member 28 and a position lever 30. The coupling member 28 provides for rotation of the drive member, typically by attachment to a motorized drive unit as described in U.S. Pat. No. 4,771,774 (the disclosure of which is incorporated herein by reference) and the position lever 30 allows the user to axially translate the drive member within the flexible tube 12. A circular cutting blade 32 is attached to the distal end of drive member 26 and is capable of being advanced past an axially elongate opening 34 formed in one side of housing 24. An inflatable balloon 36 is secured to housing 24 on a side opposite to opening 34, and the balloon may be used to urge the housing 24 against a region of atheroma so that the atheromic material enters opening 34. In this way, the cutting blade 32 may be used to sever the atheroma and translate the atheroma forward into the distal end of housing 24. As described thus far, the construction and operation of catheter 10 is generally the same as that described in European Patent Application 163 502 and U.S. Pat. No. 4,669,469, both of which have been previously incorporated herein by reference.

According to the present invention, a fixed guide wire 40 is secured to the distal tip of housing 24 and includes an axial passage or lumen 42 therethrough. The passage 42 opens into the interior 44 of housing 24, with said interior being opened into the central lumen 46 of flexible tube 12. In this way, a movable guide wire 48 may be received by the catheter 10, passing through the passageway 42, the interior 44, and the lumen 46, as illustrated. As further illustrated, the movable guide wire 48 passes through a hollow interior of the drive member 26 which in turn passes through the lumen 46 and interior 44. It will be appreciated, however, that in other constructions the drive member 26 may be absent and the movable guide wire 48 will pass directly through a wire lumen formed in the flexible tube of the catheter body.

Referring now in particular to FIG. 3, once the distal tip of catheter 10 is positioned proximate a region of atheroma A in a blood vessel BV, the movable guide wire 48 may be withdrawn, leaving the axial passage 42 and interior 44 of housing 24 free from the guide wire. Cutting member 32 may be utilized in a conventional manner to sever portions S of atheroma and deposit the portions at the distal end of the housing 24, as illustrated. The fixed guide wire 40 will then act as a trap, preventing loss of the atheroma portions S from the housing 24. This is an advantage over previous "over-the-wire" constructions where the axial passage receiving the movable guide wire in the distal housing is relatively short, exposing the patient to the danger of emboli being released from the catheter. After removal of the movable guide wire 48, fixed guide wire 40 will be able to act in a conventional manner to facilitate repositioning of the catheter 10 within the blood vessel.

The housing 24 of catheter 10 may also be adapted to carry other interventional elements, such as optical wave guides for delivering laser energy and hot caps for delivering heat. In both cases, the catheters could be utilized in heat ablation therapy where atheromic material is ablated by the direct application of heat. The housing can also be adapted for drug infusion, conveniently by releasing drugs through the fixed guide wire to itself.

Referring now to FIG. 4, a balloon catheter 50 constructed in accordance with the principles of the present invention will be described. The catheter 50 is similar in construction to the coaxial balloon catheters described in U.S. Pat. No. 4,323,071, the disclosure of which has previously been incorporated herein by reference. The catheter 50 comprises a central tube 52 and a secondary tube 54 which is expanded at its distal end to form a balloon component 56. The second tube 54 further defines an annular lumen 58 which extends to a proximal end (not shown) of the balloon in order to allow for inflation of the balloon component 56. The second tube 54 is constricted about the central tube 52 at its distal tip 60 in order to provide for sealing of the interior of balloon component 56. A central lumen 62 defined by the central tube 52 provides a wire lumen capable of receiving a movable guide wire 64 as illustrated in broken line. A fixed guide wire 66 is secured to the distal tip 60 and includes axial passage 68 which further defines the wire lumen for receiving movable guide wire 64.

Referring now to FIG. 5, an ultrasonic imaging catheter 70 constructed in accordance with the principles of the present invention will be described. Imaging catheter 70 includes flexible tube 72 and distal housing 74. An ultrasonic transducer 76 is disposed at the forward end of the interior of housing 74 and a rotating mirror 77 is disposed within the housing proximally relative to the transducer. Mirror 77 is mounted on a rotatable drive member 78.

A fixed guide wire 80 is illustrated to be detachably secured to the housing 74 and includes an axial passage 82 therethrough. A second axial passage 84 is formed in the tip of housing 74, and passages 86 and 88 are formed in both transducers 76 and mirror 77, respectively. The drive member 78 is hollow, and a movable guide wire 90 may thus be received through the entire catheter assembly 70, as illustrated. Use of a detachable fixed guide wire is advantageous as it will allow guide wires having different flexibility, length, and diameter, to be utilized as needed. The operation and construction of ultrasonic imaging catheters is described in more detail in U.S. Pat. No. 4,794,931, the disclosure of which is incorporated herein by reference.

Although the foregoing invention has been described in detail for purposes of clarity of understanding, it will be obvious that certain modifications may be practiced within the scope of the appended claims.

What is claimed is:

1. A vascular catheter comprising:
 a catheter body, including an elongate flexible tube having distal and proximal ends and a rigid housing having a proximal and secured to the distal end of the flexible tube, and having at least one lumen extending from the proximal end to the distal end thereof;
 a fixed guide wire secured to the distal end of the rigid housing, said fixed guide wire having an axial passage aligned with the one lumen so that the passage and lumen are capable of receiving a movable guide wire, said fixed guide wire having a flexible distal portion with a substantially constant diameter; and
 a movable guidewire extending through the lumen of the flexible tube and the axial passage of the fixed guidewire.

2. A vascular catheter as in claim 1, wherein the fixed guide wire is detachably secured to the rigid housing.

3. A vascular catheter as in claim 1, wherein the fixed guide wire is permanently secured to the rigid housing.

4. A vascular catheter as in claim 1, further comprising an interventional or diagnostic means disposed within the rigid housing.

5. A vascular catheter as in claim 1, further comprising a dilatation balloon coupled to the rigid housing and secured at the distal end of the flexible tube.

6. A vascular catheter as in claim 1, wherein the fixed guide wire has an external diameter in the range from about 0.016 to 0.06 inches.

7. A vascular catheter as in claim 1, wherein the fixed guide wire has an internal diameter in the range from about 0.012 to 0.04 inches.

8. A vascular catheter as in claim 1, wherein the fixed guide wire has a length in the range from about 1 to 5 cm.

9. A vascular catheter comprising:
 a catheter body, including an elongate flexible tube having distal and proximal ends and a housing having a proximal end secured to the distal end of the flexible tube, and having at least one lumen extending from the proximal end to the distal end thereof;
 a fixed guide wire secured to the distal end of the housing, said fixed guide wire having an axial passage aligned with the one lumen so that the passage and lumen are capable of receiving a movable guide wire, said fixed guide wire having a flexible distal portion with a substantially constant diameter;
 a movable guidewire extending through the lumen of the flexible tube and the axial passage of the fixed guidewire; and
 means for severing atheroma at the distal end of the catheter body.

10. A vascular catheter comprising:
 a catheter body, including an elongate flexible tube having distal and proximal ends and a housing having a proximal end secured to the distal end of the flexible tube, and having at least one lumen extending from the proximal end to the distal end thereof;
 a fixed guide wire secured to the distal end of the housing, said fixed guide wire having an axial passage aligned with the one lumen so that the passage and lumen are capable of receiving a movable guide wire, said fixed guide wire having a flexible distal portion with a substantially constant diameter;
 a movable guidewire extending through the lumen of the flexible tube and the axial passage of the fixed guidewire; and
 means for ultrasonic imaging at the distal end of the catheter body.

11. A vascular catheter comprising:
 a catheter body, including an elongate flexible tube having distal and proximal ends and a housing having a proximal end secured to the distal end of the flexible tube, and having at least one lumen extending from the proximal end to the distal end thereof;
 a fixed guide wire secured to the distal end of the housing, said fixed guide wire having an axial passage aligned with the one lumen so that the passage and lumen are capable of receiving a movable guide wire, said fixed guide wire having a flexible distal portion with a substantially constant diameter;
 a movable guidewire extending through the lumen of the flexible tube and the axial passage of the fixed guidewire; and a cutting blade, disposed within said housing, for severing atheroma.

12. A vascular catheter comprising:
    a catheter body, including an alongate flexible tube having distal and proximal ends and a housing having a proximal end secured to the distal end of the flexible tube, and having at least one lumen extending from the proximal end to the distal end thereof;
    a fixed guide wire secured to the distal end of the housing, said fixed guide wire having an axial passage aligned with the one lumen so that the passage and lumen are capable of receiving a movable guide wire, said fixed guide wire having a flexible distal portion with a substantially constant diameter;
    a movable guidewire extending through the lumen of the flexible tube and the axial passage of the fixed guidewire; and
    an ultrasonic transducer disposed within said housing.

13. A vascular catheter comprising:
    a catheter body, including an elongate flexible tube having distal and proximal ends and a rigid housing having a proximal end secured to the distal end of the flexible tube, and having at least one lumen extending from the proximal end to the distal end thereof;
    a fixed guide wire comprising a helical coil secured to the distal end of the rigid housing, said fixed guide wire having an axial passage aligned with the one lumen so that the passage and lumen are capable of receiving a movable guide wire; and
    a movable guidewire extending through the lumen of the flexible tube and the axial passage of the fixed guidewire.

14. A vascular catheter system comprising:
    a flexible tube having at least one lumen extending from a proximal to a distal end thereof;
    a housing having proximal and distal ends secured at its proximal end to the distal end of the flexible tubing;
    a fixed guide wire consisting of a helical coil having a cross-sectional area smaller than the cross-sectional area of the housing, the fixed guidewire being secured to the distal end of the housing and having an axial passage therethrough; and
    a movable guide wire extending through the lumen of the flexible tube and the axial passage of the fixed guide wire.

15. A vascular catheter as in claim 14, wherein the fixed guide wire is detachably secured to the housing.

16. A vascular catheter as in claim 14, wherein the fixed guide wire is permanently secured to the housing.

17. A vascular catheter as in claim 14, wherein the fixed guide wire has an external diameter in the range from about 0.016 to 0.06 inches.

18. A vascular catheter as in claim 14, wherein the fixed guide wire has an internal diameter in the range from about 0.012 to 0.04 inches.

19. A vascular catheter as in claim 14, wherein the fixed guide wire has a length in the range from about 1 to 5 cm.

20. A vascular catheter system comprising:
    a flexible tube having proximal and distal ends and at least one lumen extending from the proximal to the distal end thereof;
    a housing having proximal and distal ends, said housing being secured at its proximal end to the distal end of the flexible tubing;
    a fixed guide wire consisting of a helical coil secured to the distal end of the housing and having an axial passage therethrough aligned with the one lumen so that the passage and lumen are capable of receiving a movable guide wire, said fixed guide wire having a flexible distal portion with a substantially constant diameter;
    a movable guide wire extending through the lumen of the flexible tube and the axial passage of the fixed guide wire; and
    an interventional means disposed within the housing.

21. A vascular catheter as in claim 20, wherein the interventional means is a cutting blade disposed within said housing.

22. A vascular catheter as in claim 20, wherein the interventional means is an ultrasonic transducer disposed within said housing.

23. A vascular catheter comprising:
    a flexible tube having proximal and distal ends and at least one lumen extending from the proximal to the distal end thereof;
    a housing having proximal and distal ends, said housing being secured at its proximal end to the distal end of the flexible tubing;
    a fixed guide wire consisting of a helical coil having a cross-sectional area smaller that the cross-sectional area of the housing, the fixed guidewire being secured to the distal end of the housing and having an axial passage therethrough;
    a movable guide wire extending through the lumen of the flexible tube and the axial passage of the fixed guide wire; and
    a dilatation balloon coupled to said housing and secured at the distal end of the flexible tube.

24. A vascular catheter comprising:
    a flexible tube having proximal and distal ends and at least one lumen extending from the proximal to the distal end thereof;
    a housing having proximal and distal ends secured at its proximal end at the distal end of the flexible tubing;
    a fixed guide wire consisting of a helical coil secured to the distal end of the housing and having an axial passage therethrough;
    a movable guide wire extending through the lumen of the flexible tube and the axial passage of the fixed guide wire; and
    means for severing atheroma disposed within said housing and secured to the distal end of the flexible tube.

25. A vascular catheter comprising:
    a flexible tube having proximal and distal ends and at least one lumen extending from the proximal to the distal end thereof;
    a housing having proximal and distal ends, said housing being secured at its proximal end to the distal end of the flexible tubing;
    a fixed guide wire consisting of a helical coil secured to the distal end of the housing and having an axial passage therethrough;
    a movable guide wire extending through the lumen of the flexible tube and the axial passage of the fixed guide wire; and means for ultrasonic imaging disposed within said housing and secured to the distal end of the flexible tube.

26. A vascular catheter comprising:
a flexible tube having at least one lumen extending from a proximal to a distal end thereof;
a housing having proximal and distal ends secured at its proximal end to the distal end of the flexible tube;
a drive member extending within the lumen of the flexible tube from its proximal end to the housing, said drive member being capable of both axial and rotational movement relative to the housing;
an interventional element secured to the drive member within the housing, said drive member and interventional element together defining an elongate passageway capable of receiving a movable guide wire; and
a fixed guide wire consisting of a helical coil secured to the distal end of the housing, said guide wire having an elongate passage therethrough which is aligned with the passage through the drive member and interventional element and capable of receiving a movable guide wire.

27. A vascular catheter as in claim 26, wherein the fixed guide wire has an external diameter in the range from about 0.016 to 0.06 inches.

28. A vascular catheter as in claim 26, wherein the fixed guide wire has an internal diameter in the range from about 0.012 to 0.04 inches.

29. A vascular catheter as in claim 26, wherein the fixed guide wire has a length in the range from bout 1 to 5 cm.

30. A vascular catheter as in claim 26, wherein the fixed guide wire is detachably secured to the housing.

31. A vascular catheter as in claim 26, further comprising means for severing atheroma proximate the housing.

32. A method for introducing a vascular catheter to a patient, said method comprising:
positioning a movable guide wire so that its distal end lies proximate a preselected location within the patient's vascular system;
introducing the vascular catheter over said movable guide wire, wherein said vascular catheter includes a fixed guide wire at its distal end, said fixed guide wire having an elongate passage therethrough which receives the movable guide wire;
withdrawing the movable guide wire after the vascular catheter has been introduced; and
repositioning the vascular catheter using the fixed guide wire after the movable guide wire has been withdrawn.

33. A method as in claim 32, further comprising performing an interventional or diagnostic procedure at the preselected location within the vascular system using the vascular catheter.

34. A method as in claim 33, wherein the interventional procedure comprises drug infusion.

35. A method as in claim 33, wherein the interventional procedure comprises severing atheroma with a blade within the housing, wherein at least a portion of the severed atheroma is trapped within the elongate passage of the fixed guide wire.

36. A method for introducing a vascular catheter to a patient, said method comprising:
positioning a movable guide wire having a distal end so that the distal end lies proximal a preselected location within the patient's vascular system;
introducing the vascular catheter over said movable guide wire, wherein said vascular catheter includes a distal end having a fixed guide wire secured thereat, said fixed guide wire having an elongate passage therethrough which receives the movable guide wire;
withdrawing the movable guide wire after the vascular catheter has been introduced;
repositioning the vascular catheter using the fixed guide wire after the movable guide wire has been withdrawn; and
severing atheroma at the preselected location within the vascular system using the vascular catheter.

37. A method for introducing a vascular catheter to a patient, said method comprising:
positioning a movable guide wire having a distal end so that the distal end lies proximal a preselected location within the patient's vascular system;
introducing the vascular catheter over said movable guide wire, wherein said vascular catheter includes a distal end having a fixed guide wire secured thereat, said fixed guide wire having an elongate passage therethrough which receives the movable guide wire;
withdrawing the movable guide wire after the vascular catheter has been introduced;
repositioning the vascular catheter using the fixed guide wire after the movable guide wire has been withdrawn; and
dilatating atheroma at the preselected location within the vascular system using the vascular catheter.

38. A method for introducing a vascular catheter to a patient, said method comprising:
positioning a movable guide wire having a distal end so that the distal end lies proximal a preselected location within the patient's vascular system;
introducing the vascular catheter over said movable guide wire, wherein said vascular catheter includes a distal end having a fixed guide wire secured thereat, said fixed guide wire having an elongate passage therethrough which receives the movable guide wire;
withdrawing the movable guide wire after the vascular catheter has been introduced;
repositioning the vascular catheter using the fixed guide wire after the movable guide wire has been withdrawn; and
imaging atheroma at the preselected location within the vascular system using the vascular catheter.

39. A vascular catheter comprising:
a catheter body, including an elongate flexible tube having distal and proximal ends and a housing having a proximal end secured to the distal end of the flexible tube, and having at least one lumen extending from the proximal end to the distal end thereof;
a fixed guide wire comprising a helical coil secured to the distal end of the housing, said fixed guide wire having an axial passage aligned with the one lumen so that the passage and lumen are capable of receiving a movable guide wire, said fixed guide wire having a flexible distal portion with a substantially constant diameter;

a movable guidewire extending through the lumen of the flexible tube and the axial passage of the fixed guidewire; and means for ultrasonic imaging at the distal end of the catheter body.

40. A vascular catheter comprising:

a catheter body, including an elongate flexible tube having distal and proximal ends and a housing having a proximal end secured to the distal end of the flexible tube, and having at least one lumen extending from the proximal end to the distal end thereof;

a fixed guide wire comprising a helical coil secured to the distal end of the housing, said fixed guide wire having an axial passage aligned with the one lumen so that the passage and lumen are capable of receiving a movable guide wire, said fixed guide wire having a flexible distal portion with a substantially constant diameter;

a movable guidewire extending through the lumen of the flexible tube and the axial passage of the fixed guidewire; and a cutting blade, disposed within said housing, for severing atheroma.

41. A vascular catheter comprising:

a catheter body, including an elongate flexible tube having distal and proximal ends and a housing having a proximal end secured to the distal end of the flexible tube, and having at least one lumen extending from the proximal end to the distal end thereof;

a fixed guide wire comprising a helical coil secured to the distal end of the housing, said fixed guide wire having an axial passage aligned with the one lumen so that the passage and lumen are capable of receiving a movable guide wire, said fixed guide wire having a flexible distal portion with a substantially constant diameter;

a movable guidewire extending through the lumen of the flexible tube and the axial passage of the fixed guidewire; and an ultrasonic transducer disposed within said housing.

* * * * *